United States Patent
Nordstrom et al.

(10) Patent No.: US 10,345,273 B2
(45) Date of Patent: Jul. 9, 2019

(54) METHODS AND APPARATUS TO VERIFY OPERATION OF ACOUSTIC EMISSION SENSORS

(71) Applicant: Fisher Controls International LLC, Marshalltown, IA (US)

(72) Inventors: Richard Allen Nordstrom, Marshalltown, IA (US); Bret Anthony Dahme, Marshalltown, IA (US); Shannon Eugene Jelken, Marshalltown, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 0 days.

(21) Appl. No.: 15/387,341

(22) Filed: Dec. 21, 2016

(65) Prior Publication Data

US 2017/0199162 A1   Jul. 13, 2017

Related U.S. Application Data

(63) Continuation-in-part of application No. 15/333,658, filed on Oct. 25, 2016, now Pat. No. 10,161,919, and
(Continued)

(51) Int. Cl.
*G01N 29/30* (2006.01)
*G01N 29/14* (2006.01)
*G01N 29/44* (2006.01)

(52) U.S. Cl.
CPC .............. *G01N 29/30* (2013.01); *G01N 29/14* (2013.01); *G01N 29/4436* (2013.01); *G01N 2291/101* (2013.01)

(58) Field of Classification Search
CPC .... G01N 29/14; G01N 29/30; G01N 29/4427; G01N 29/4436; G01N 29/28; G01N 2291/101; G01H 3/00; G01V 13/00
(Continued)

(56) References Cited

U.S. PATENT DOCUMENTS 3,325,781 A   6/1967   Harris
3,546,924 A   12/1970  Nussbaum et al.
(Continued)

FOREIGN PATENT DOCUMENTS

DE   10153297     4/2003
DE   202009014773  3/2011
(Continued)

OTHER PUBLICATIONS

United States Patent and Trademark Office, "Non-Final Office Action," issued in connection with U.S. Appl. No. 14/992,755, dated Jan. 18, 2018, 23 pages.
(Continued)

*Primary Examiner* — Lisa M Caputo
*Assistant Examiner* — Rose M Miller
(74) *Attorney, Agent, or Firm* — Hanley, Flight and Zimmerman, LLC

(57) ABSTRACT

Methods and apparatus verify operation of acoustic emission sensors are disclosed. A disclosed example apparatus includes an acoustic source acoustically coupled to a device, where the acoustic source is to generate an acoustic signal, and a processor to determine an operational condition of an acoustic emission sensor associated with the device based on measuring the generated acoustic signal at the acoustic emission sensor.

17 Claims, 5 Drawing Sheets

Related U.S. Application Data a continuation-in-part of application No. 14/992,755, filed on Jan. 11, 2016, now Pat. No. 10,161,912.

(58) Field of Classification Search
USPC ........ 73/587, 1.82, 590, 592, 593, 584, 1.84
See application file for complete search history.

(56) References Cited

U.S. PATENT DOCUMENTS

| | | | |
|---|---|---|---|
| 4,011,472 A | | 3/1977 | Feng |
| 4,043,176 A | * | 8/1977 | Graham ............. G01N 29/2437 73/1.82 |
| 4,043,180 A | * | 8/1977 | Morris .................. E21B 47/101 340/515 |
| 4,437,332 A | | 3/1984 | Pittaro |
| 4,519,251 A | | 5/1985 | Dickson |
| 4,567,770 A | | 2/1986 | Rumbold et al. |
| 5,005,415 A | | 4/1991 | Holroyd |
| 5,101,162 A | * | 3/1992 | Webster ................ G01H 3/005 324/537 |
| 5,156,050 A | | 10/1992 | Schmid et al. |
| 5,191,796 A | * | 3/1993 | Kishi ...................... B06B 1/06 310/336 |
| 5,435,168 A | * | 7/1995 | Granere .................. G01P 21/00 73/1.84 |
| 5,629,906 A | | 5/1997 | Sudol et al. |
| 6,016,701 A | | 1/2000 | McClelland et al. |
| 6,672,131 B1 | * | 1/2004 | Aldal ...................... G01F 1/667 73/1.82 |
| 8,037,762 B2 | | 10/2011 | La Rosa Flores et al. |
| 8,311,759 B2 | * | 11/2012 | Sutherland .............. F16L 55/48 367/117 |
| 10,161,912 B2 | | 12/2018 | Nordstrom et al. |
| 10,161,919 B2 | | 12/2018 | Dahme et al. |
| 2001/0007203 A1 | * | 7/2001 | Goodman ............ G01N 29/045 73/1.82 |
| 2007/0034012 A1 | * | 2/2007 | Amir ....................... G01M 7/00 73/627 |
| 2010/0089161 A1 | * | 4/2010 | Taheri .................. G01M 7/025 73/588 |
| 2010/0218591 A1 | * | 9/2010 | Rhodes et al. .......... G01F 1/666 73/1.82 |
| 2016/0178478 A1 | * | 6/2016 | Erskine .................. G01L 25/00 73/593 |
| 2017/0199161 A1 | | 7/2017 | Nordstrom et al. |
| 2017/0199162 A1 | | 7/2017 | Nordstrom et al. |

FOREIGN PATENT DOCUMENTS

| | | |
|---|---|---|
| EP | 0727259 | 8/1996 |
| JP | S5767853 | 4/1982 |
| JP | H0194258 | 4/1989 |
| KR | 20080102082 | 11/2008 |
| WO | 2011050992 | 5/2011 |
| WO | 2017123567 | 7/2017 |

OTHER PUBLICATIONS

United States Patent and Trademark Office, "Non-Final Office Action," issued in connection with U.S. Appl. No. 15/333,658, dated Jan. 17, 2018, 22 pages.

United States Patent and Trademark Office, "Notice of Allowance," issued in connection with U.S. Appl. No. 15/333,658, dated Apr. 10, 2016, 17 pages.

United States Patent and Trademark Office, "Notice of Allowance and Fee(s) Due," issued in connection with U.S. Appl. No. 14/992,755, dated May 22, 2018, 21 pages.

International Searching Authority, "International Search Report," issued in connection with International Application No. PCT/US2017/057956, dated Jan. 26, 2018, 6 pages.

International Searching Authority, "Written Opinion," issued in connection with International Application No. PCT/US2017/057956, dated Jan. 26, 2018, 8 pages.

International Searching Authority, "Written Opinion of the International Searching Authority," issued in connection with International Application No. PCT/US2017/057957, dated Jan. 26, 2018, 7 pages.

International Searhing Authority, "International Search Report," issued in connection with International Application No. PCT/US2017/057957, dated Jan. 26, 2018, 6 pages.

United States Patent and Trademark Office, "Requirement for Restriction/Election," issued in connection with U.S. Appl. No. 14/992,755, dated Oct. 5, 2017, 7 pages.

United States Patent and Trademark Office, "Notice of Allowance," in connection with U.S. Appl. No. 15/133,658, dated Sep. 12, 2018, 17 pages.

United States Patent and Trademark Office, "Notice of Allowance," in connection with U.S. Appl. No. 14/992,755, dated Sep. 20, 2018, 16 pages.

\* cited by examiner

METHODS AND APPARATUS TO VERIFY OPERATION OF ACOUSTIC EMISSION SENSORS

RELATED APPLICATIONS

This patent arises as a continuation-in-part of U.S. application Ser. No. 14/992,755, which was filed on Jan. 11, 2016, and U.S. application Ser. No. 15/333,658, which was filed on Oct. 25, 2016, both of which are hereby incorporated by reference in their entireties.

FIELD OF THE DISCLOSURE

This disclosure relates generally to acoustic emission sensors and, more particularly, to methods and apparatus to verify operation of acoustic emission sensors.

BACKGROUND

Acoustic emission sensors are typically used in known monitoring systems to monitor an operational status of a device (e.g., a valve or other process control device) to which an acoustic emission sensor is coupled. In some known examples, the acoustic emission sensor is monitored to determine whether the acoustic emission sensor is functioning properly and, as a result, whether measurements from the acoustic emission sensor are accurate. One known method of verifying this functionality is a pencil lead break test that involves a person (e.g., an operator or technician) breaking lead from a mechanical pencil adjacent the acoustic emission sensor. Another known test involves using piezoelectric sensors in a reciprocity mode. However, these known tests do not meet the reproducibility and/or practical implementation requirements needed to properly assess the acoustic emission sensor and can also cause an operator or technician to improperly assess the functionality of the acoustic emission sensor.

SUMMARY

An example apparatus includes an acoustic source acoustically coupled to a device, where the acoustic source is to generate an acoustic signal, and a processor to determine an operational condition of an acoustic emission sensor associated with the device based on measuring the generated acoustic signal at the acoustic emission sensor.

An example method includes generating an acoustic signal at an acoustic source that is acoustically coupled to a device, and measuring, at an acoustic emission sensor that is operatively coupled to the device, the acoustic signal. The example method also includes determining, using a processor, an operating condition of the acoustic emission sensor based on the acoustic signal.

An example tangible machine readable medium includes instructions, which when executed, cause a processor to at least cause an acoustic source to generate an acoustic signal and compare a signal measured at an acoustic emission sensor that is acoustically coupled to the acoustic source to a baseline to determine a condition of the acoustic emission sensor, where the measured signal is to correspond to the generated acoustic signal.

Figure 1:
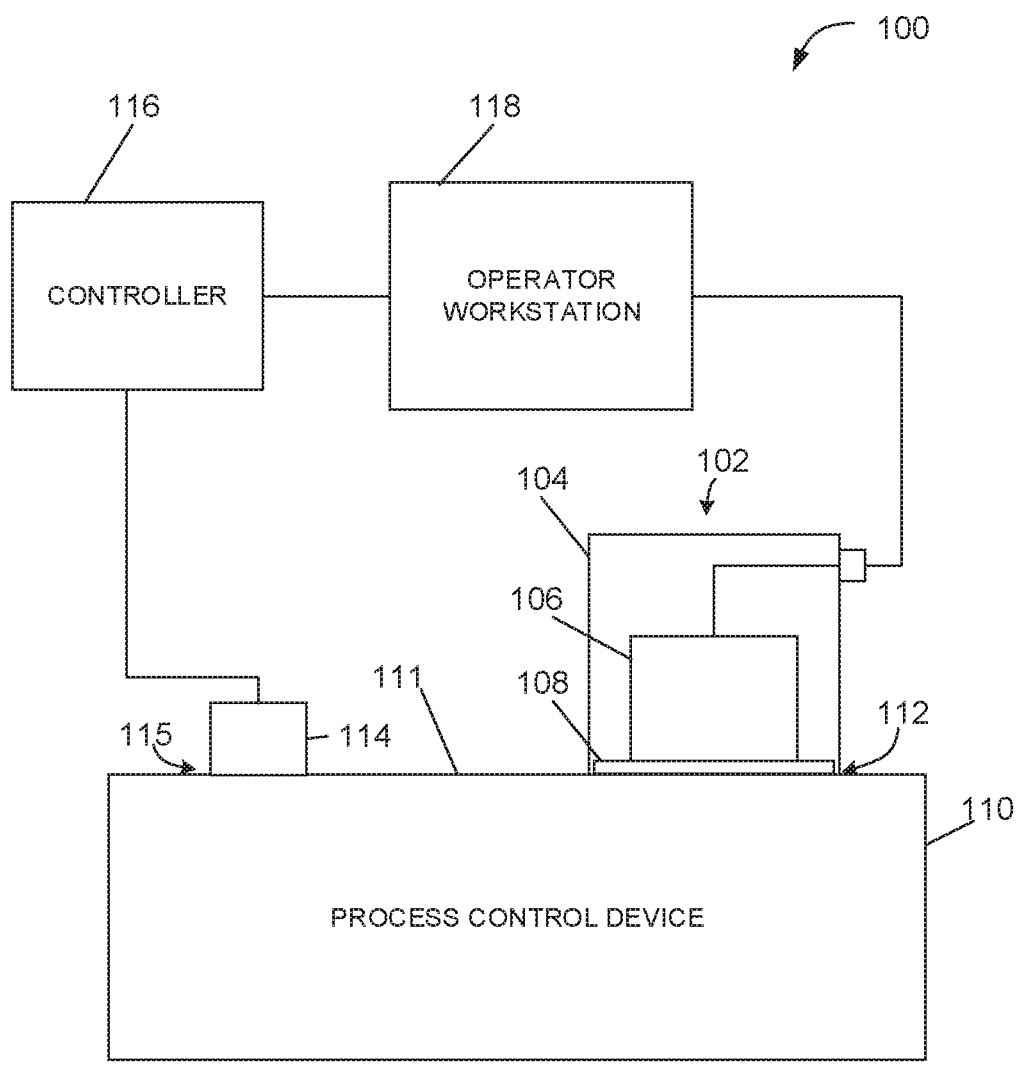
FIG. 1 is a diagram of an example acoustic test apparatus that may be implemented to test an operational condition of an acoustic emission sensor.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

Methods and apparatus to verify operation of acoustic emission sensors are disclosed. Acoustic emission sensors are typically used to verify an operation and/or operational status of a device (e.g., a process control device). As a result, the functionality of the acoustic emission sensor is verified to ensure that data collected from the acoustic emission sensor is precise and/or accurate. Therefore, some known testing/monitoring systems utilize a lead break test. Other known testing/monitoring systems utilize multiple acoustic emission sensors and/or piezoelectric devices to verify operation of the acoustic emission sensor.

The examples disclosed herein provide an accurate and cost-effective way of characterizing an operating status or condition of an acoustic emissions sensor and/or a data chain associated with the acoustic emission sensor. In particular, the examples disclosed herein utilize an acoustic source (e.g., a DC motor, an asymmetric motor, a piezoelectric device, a resonator, a tuning fork, etc.) and/or an appropriate haptic device to generate an acoustic signal that is measured at the acoustic emissions sensor of interest. The measured signal can be compared to a baseline (e.g., a baseline signal, a recorded baseline signal, etc.), which may include a threshold value and/or an expected waveform. The examples used herein utilize acoustic sources (e.g., simulated acoustic emission sources) such as motors, turning forks, resonators and/or other haptic devices, which are relatively inexpensive and uncomplicated to implement. The examples disclosed herein mount the acoustic source in a housing and/or enclosure to ensure reliable mechanical and acoustic coupling.

As used herein, the term "motor" may refer to a motor with an asymmetric counterweight or any appropriate haptic devices and/or vibrational devices that generate acoustic wave sources or vibrations. As used herein, the term "waveform" refers to any type of electrical signal, which may or may not be normalized (e.g., unitless).

FIG. 1 is a diagram of an acoustic test apparatus 100 that may be implemented to test an operational condition of an acoustic emission sensor 102, which may be, for example, commercially available (e.g., a Vallen System acoustic emission sensor). The example acoustic emission sensor 102 includes a housing 104 and a piezoelectric element 106 disposed in and/or at least partially surrounded by the housing 104. The example acoustic emission sensor 102 also includes a wear plate 108 coupled to the housing 104. The wear plate 108 of the illustrated example is at least partially surrounded by the housing 104 and protects (e.g., prevents damage to) the piezoelectric element 106. In some examples, other components (e.g., an electrode, damping material, etc.) may also be disposed within the housing 104. The acoustic test apparatus 100 also includes an example process control device 110, which may be a valve, a pipe, or any other process control device. The acoustic emission sensor 102 is operatively coupled to a surface 111 of the process control device 110 via the wear plate 108, and is disposed proximate the process control device 110 to create an acoustic path by facilitating propagation of acoustic signals to the acoustic emission sensor 102. In the illustrated example of FIG. 1, an acoustic source 114, which is implemented as a motor (e.g., a motor assembly, a haptic motor, direct-current (DC) motor, a brushless motor, etc.) in this example. In particular, the acoustic source 114 is implemented as an asymmetric motor in this example and communicatively coupled to the process control device 110.

To facilitate acoustic coupling/attachment of the acoustic emission sensor 102 to the surface 111 by, a coupling agent or layer 112 such as, for example, a liquid, a gel, or any other suitable coupling agent may be used. In some examples, the use of a liquid or gel as the coupling layer 112 may improve the acoustic coupling by decreasing the amount of air gaps that would otherwise occur between the wear plate 108 and the surface 111. In some other examples, the coupling agent or layer 112 may include a glue or partial glue-filler combination capable of providing stable acoustic coupling for long term use.

According to the illustrated example, to couple the motor 114 to the process control device 110, a coupling agent or layer 115 (e.g., a liquid or gel) is used. In some examples, the type of coupling agent or layer 112, 115 used to couple the acoustic emission sensor 102 and/or the motor to the surface 111 of the process control device 110 affects the quality of the acoustic path therebetween. Alternatively, the acoustic emission sensor 102 and/or the motor 114 may be coupled to the process control device 110 without a coupling agent or layer 112, 115 using, for example, a mechanical fastener, a magnetic coupling, etc.

The acoustic test apparatus 100 also includes an example controller 116 and an operator workstation 118. The operator workstation 118 may be operatively coupled to the controller 116 and/or the acoustic emission sensor 102.

In operation, to control and/or vary an output signal to the motor 114, the example controller 116 is operatively coupled to the motor 114 to provide an electrical signal (e.g., a voltage signal) to the motor 114. Additionally or alternatively, data pertinent to the output signal (e.g., defined output functions) may be stored on a storage device of the controller 116 and/or the operator workstation 118 to facilitate remote access. In some examples, the electrical signal (e.g., input voltage signal sent to the motor 114) may be varied to produce different corresponding acoustic signals (e.g., output acoustic signals from the motor 114). For example, the acoustic signal may be varied in amplitude, frequency, pulse duration or duty cycle, etc. by the example controller 116. In other words, characteristics of the acoustic signal waveform may be varied to suit the needs of a particular application.

To determine a functional and/or operating condition of the process control device 110 (e.g., to detect leaks in the process control device 110) and/or monitor the structural health of the process control device 110, the acoustic emission sensor 102 measures acoustic signals and transmits the measured acoustic signals using an analog communication interface. The piezoelectric element 106 may be operative to detect mechanical movement resulting in an acoustic signal. For example, the piezoelectric element 106 of the acoustic emission sensor 102, which may be coupled to a valve or pipe, is operative to detect leaks in the valve or pipe. Additionally or alternatively, the acoustic emission sensor 102 can detect any other events and/or operational conditions corresponding to the process control device 110.

According to the illustrated example, to test operation, a condition and/or functionality of the acoustic emission sensor 102, an electrical signal (e.g., the voltage signal) is provided (e.g., transmitted) to the motor 114 to produce a specific acoustic output signal which, in turn, is measured by the acoustic emission sensor 102. To identify and/or characterize the acoustic signals from the motor 114 that are measured at the acoustic emission sensor 102 so that an assessment of the operating condition of the acoustic emission sensor may be made, data associating the electrical signals to the acoustic signals output by the motor 114 are stored in a database. In some examples, the data is organized in a table, a chart, a graph, etc. The data may include acoustic reference signals corresponding to the electrical signals and/or the expected acoustic signals from the motor 114 so that conditional determinations of the acoustic emission sensor 102 may be made. Additionally, the data may be accessed remotely from an operator workstation such as, for example, the example operator work station 118. In some examples, the acoustic emission sensor 102 may transmit the measured acoustic signal to the controller 116 and/or a second controller (e.g., a data acquisition system). The example controller 116 and/or the second controller may be operative to store and/or analyze the data (e.g., measured acoustic signals).

In this example, the acoustic signal measured by the acoustic emission sensor 102 (e.g., the measured acoustic signal) is compared to data representing a reference/baseline acoustic signal. The data representing a reference acoustic signal may be stored in, for example, a table, a chart, or a graph that indicates the expected acoustic signal measured by the acoustic emission sensor 102 for each possible electrical signal sent to the motor 114. In some examples, the reference acoustic signal is a previous signal (e.g., an initial signal, an original signal, a calibration signal, etc.) that was output by the motor 114 and measured by the acoustic emission sensor 102. In some examples, the previous signal is used to track and/or characterize the acoustic emission sensor 102 and/or degradation of the acoustic emission sensor 102. Alternatively, the reference acoustic signal may be equivalent to the acoustic signal output by the motor 114. A deviation between the measured acoustic signal and the reference acoustic signal is determined based on a comparison between the measured acoustic signal and the data representing the reference acoustic signal. In some examples, the deviation is determined by comparing the values of the amplitudes of the reference signal and the measured acoustic signal. The deviation may be represented as a numerical value equivalent to the difference between the two amplitudes or as a percentage difference between the measured acoustic signal and the reference acoustic signal.

To characterize the acoustic signal from measured by the acoustic emission sensor 102, a functionality or operational condition of the acoustic emission sensor 102 may be determined or assessed based on the deviation between the measured acoustic signal and the reference acoustic signal. The deviation between the measured acoustic signal and the reference acoustic signal may indicate an accuracy of measurements from the acoustic emission sensor 102 and/or the functionality of the acoustic emission sensor 102. For example, if the deviation between the measured acoustic signal and the reference acoustic signal is greater than a threshold, the acoustic emission sensor 102 may need maintenance, repair or replacement. The acoustic emission sensor 102 may be designated as not functional if the difference between the measured acoustic signal and the reference acoustic signal is greater than a certain percentage (e.g., 5%). An alert or alarm may be displayed via the operator workstation 118 indicating that the acoustic emission sensor 102 is malfunctioning. If the difference between the measured acoustic signal and the reference acoustic signal is less than the threshold, the acoustic emission sensor 102 may be considered to be functioning properly and not requiring repair or replacement. Additionally or alternatively, if a waveform and/or overall shape (e.g., a time-history shape) does not match a known expected waveform, the acoustic emission sensor 102 may be deemed to be malfunctioning. An appropriate message may be transmitted to the operator workstation 118 indicating the operational condition of the acoustic emission sensor 102.

Electrical signals may be communicated to the motor 114 via any suitable wired or wireless connection. In some examples, the electrical signal (e.g., electrical input) is provided over the same connection connecting the acoustic emission sensor 102 to the database (e.g., to a data logging system). Alternatively, any other suitable means of communicating an electrical signal to the motor 114 may be implemented instead. In some examples, the controller 116 is also communicatively coupled to the process control device 110 via any suitable wired or wireless connection.

In some examples, the operator workstation 118 communicates with the controller 116, the acoustic emission sensor 102, and/or any other controllers or data acquisition systems via a wired or wireless communication protocol. For example, the operator workstation 118 may be remotely located (e.g., a location miles away) from the controller 116, the acoustic emission sensor 102, and/or any other controllers and may communicate via a wireless protocol to access data, trigger a check of the acoustic emissions sensor 102, and/or perform diagnostic tests if any inconsistencies are detected within the system. The example acoustic emission sensor 102 may transmit measured acoustic signal data using an analog signal. Alternatively, any other suitable form of wired or wireless communication (e.g., analog or digital) may be used. In some examples, the electrical signal provided to the motor 114 may be determined and/or selected by an operator via the operator workstation 118 and/or the controller 116. For example, the operator may determine a magnitude, frequency and/or timed pattern (e.g., a pulsed pattern) of the voltage of the electrical signal sent to the motor 114. Additionally, the operator may determine a time at which to send the electrical signal to the motor 114.

In some examples, the operator determines the times at which the electrical signal is sent to the motor 114 via the operator workstation 118 by defining a test schedule. Alternatively, the operator can manually send an electrical signal to the motor 114 (e.g., send an electrical signal on demand) via the operator workstation 118 and/or the controller 116 when the acoustic emission sensor 102 is to be tested. The operator may use the operator workstation 118 to create a test schedule to be followed by the controller 116. In some examples, the test schedule indicates a specific time each day at which the controller 116 is to send an electrical signal to the motor 114. In this manner, the electrical signal is transmitted to the motor 114 at the designated time(s) (e.g., the scheduled time(s)) without further input from the operator). In some examples, the schedule indicates that a test of the acoustic emission sensor 102 is performed on a weekly, monthly, or yearly basis. A test and/or measurement of an acoustic signal received by the acoustic emissions sensor may also be triggered by an event in the process control system such as, for example, a valve closing or opening. Transmitting the electrical signal to the motor 114 may include transmitting electrical pulses for a time period specified by an operator. Alternatively, the operator commands the controller 116 to continuously provide the motor 114 with an electrical signal. In such examples, the operator may designate a stop time or provide the motor 114 with an electrical signal (e.g., continuously) until the operator instructs the controller 116 to stop.

In some examples, the acoustic signal data measured by the acoustic emission sensor 102 is filtered to improve detection of the acoustic signal by the acoustic emission sensor 102. In some examples, the testing of the acoustic emission sensor 102 is triggered by the controller 116 detecting an error and/or possible malfunction of the acoustic emission sensor 102.

Figure 2:
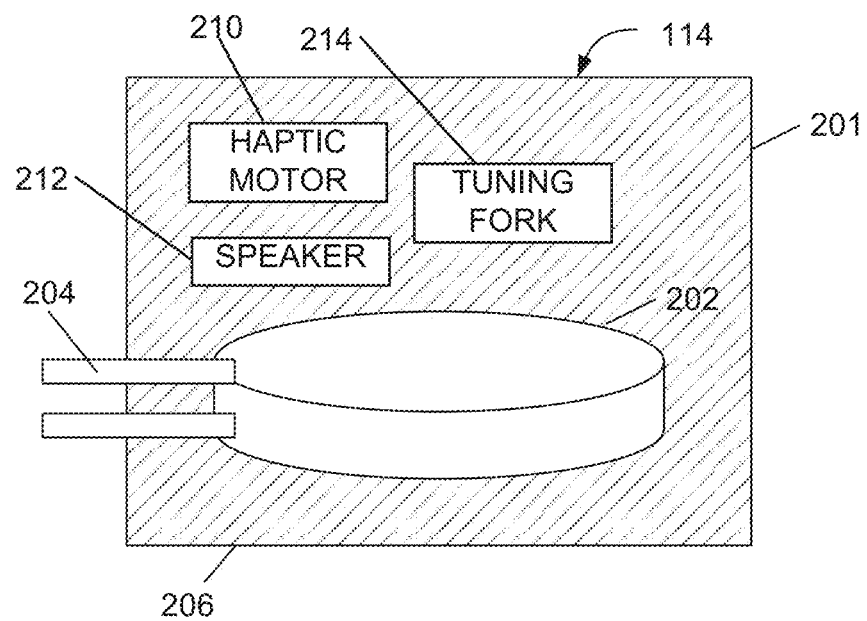
FIG. 2 is a cross-sectional view of an acoustic source, which is implemented as a motor in this example, in accordance with the teachings of this disclosure.

FIG. 2 is a detailed cross-sectional view of the example motor assembly 114. As can be seen in the illustrated view of FIG. 2, the motor 114 includes a mount (e.g., a coupling interface) or housing, which is implemented as an overmold (e.g., a potting material, a polymer, a silicone polymer, a neoprene mount, etc.) 201 that encases an electrical motor component (e.g., a DC motor, a haptic motor) 202. In this example, electrical wires 204 penetrate the overmold 201 to electrically couple electric motor component 202 and/or the motor 114 to the example controller 116. Alternatively, in some examples, the wires 204 are implemented as a single integrated wire that is electrically coupled to the motor component 202.

In this example, a surface 206 of the overmold 201 is coupled to and/or affixed to the controller process control device 110 at the surface 111. In particular, in some examples, the overmold 201 is pressed against the surface 111 to ensure suitable acoustic coupling between the electric motor 114 and the acoustic emissions sensor 102. As mentioned above in connection with FIG. 1, the surface 206 may be adhered to the surface 111. In some examples, the overmold 201 may be elastically deformable so that the motor 114 and/or the overmold 201 can be coupled to and/or pressed against irregular, contoured and/or round surfaces to conform to these surfaces.

While the example overmold 201 is shown in a generally rectangular shape in this example, the overmold 201 may be any appropriate shape such as, but not limited to, round, cylindrical, circular, pentagonal, hexagonal, etc. Additionally or alternatively, the overmold 201 can surround/envelope a haptic motor 210, a speaker 212 or a turning fork 214, as can be seen in FIG. 2. In some examples, the haptic motor 210, the speaker 212 or the tuning fork 214 are embedded within the overmold 201, which can be implemented using a polymer (e.g., a polymer overmold).

While the motor 114 of the illustrated example is implemented as an electric motor, an alternate acoustic source may be used including, but not limited to, a haptic device, a piezoelectric device, a speaker, a subwoofer, a tuning fork and/or a resonator. Further, any appropriate acoustic source that generates acoustic energy and/or waves may be used.

Any of the described acoustic sources may be molded within and/or encased in a polymer material.

Figure 3:
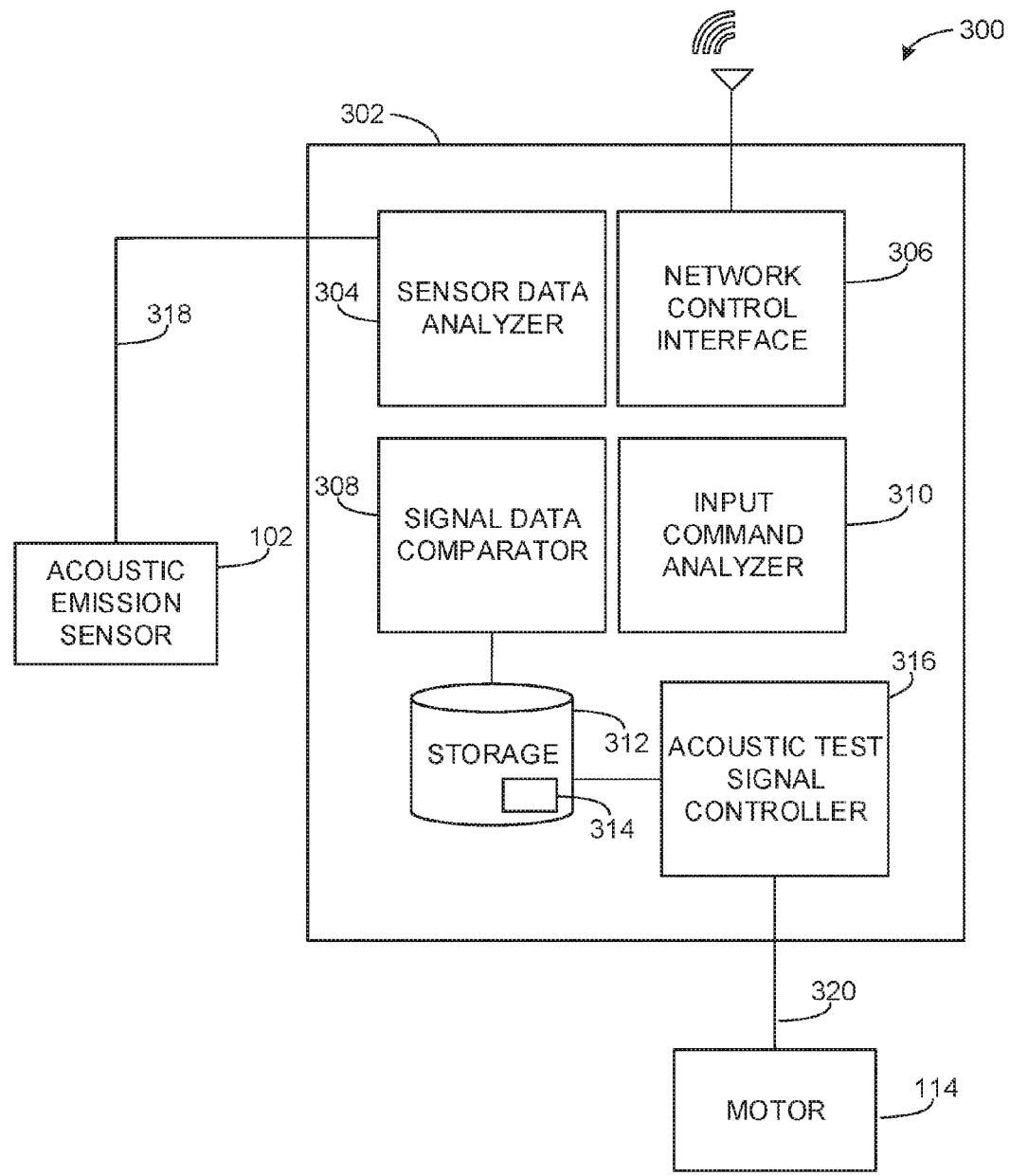
FIG. 3 is a schematic overview of an example acoustic signal analysis system that may be implemented with the examples disclosed herein.

FIG. 3 is a schematic overview of an acoustic signal analysis system 300 that may be implemented with the examples disclosed herein. In particular, the acoustic signal analysis system 300 is a computational system may be implemented in the controller 116 and/or the operator workstation 118 to verify or characterize a coupling of the acoustic emission sensor 102 and/or an operating condition of the acoustic emission sensor 102. The acoustic signal analysis system 300 includes an analyzer 302, which includes a sensor data analyzer 304, a network control interface 306, a signal data comparator 308, an input command analyzer 310, storage 312 with stored acoustic data 314 and an acoustic test signal controller 316. In this example, the sensor data analyzer 304 is communicatively coupled to the acoustic emission sensor 102 via a communication line 318 and the acoustic test signal controller 316 is communicatively coupled to the motor 114 via a communication line 320.

To verify an operational or functional status of the acoustic emission sensor 102, the acoustic test signal controller 316 of the illustrated example directs the motor 114 to generate an output signal by providing a corresponding electrical signal/voltage to the motor 114. As a result, the example acoustic emission sensor 102, which is acoustically coupled to the motor 114, measures and/or detects a corresponding signal (e.g., acoustic and/or vibrational signal) and, in turn, forwards the signal to the example sensor data analyzer 304. According to the illustrated example, the sensor data analyzer 304 analyzes and/or converts/compiles the data so that the signal data comparator 308 can compare the measured data from the acoustic emission sensor 102 with the stored acoustic data 314. In particular, the signal data comparator 308 may compared the measured data to a threshold and/or an expected waveform or signal pattern, which may be received and/or updated via the network control interface 306, for example. In some examples, the sensor data analyzer 304 and/or the signal data comparator 308 causes the network control interface 306 to send a message to the controller 116 and/or the operator workstation 118 indicating that the acoustic emission sensor 102 is operating normally (e.g., within specifications) or malfunctioning.

In some examples, the input command analyzer 310 receives an input command from the operator workstation 118 to initiate testing of the acoustic emission sensor 102. In some examples, the output signal generated by the motor 114 may be varied in amplitude, frequency and/or pulse duration(s) so that a measured signal at the acoustic emission sensor 102 can be compared to a characteristic expected measured signal that corresponds to the variances in the amplitude, the frequency and/or the pulse duration(s). In some examples, the motor 114 may transmit signals between 10 kilohertz (kHz) to 1 megahertz (MHz).

While an example manner of implementing the acoustic signal analysis system 300 of FIG. 3 is illustrated in FIG. 3, one or more of the elements, processes and/or devices illustrated in FIG. 3 may be combined, divided, re-arranged, omitted, eliminated and/or implemented in any other way. Further, the example sensor data analyzer 304, the example network control interface 306, the example signal data comparator 308, the example input command analyzer 310, the example acoustic test signal controller 316 and/or, more generally, the example acoustic signal analysis system 300 of FIG. 3 may be implemented by hardware, software, firmware and/or any combination of hardware, software and/or firmware. Thus, for example, any of the example sensor data analyzer 304, the example network control interface 306, the example signal data comparator 308, the example input command analyzer 310, the example acoustic test signal controller 316 and/or, more generally, the example acoustic signal analysis system 300 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example sensor data analyzer 304, the example network control interface 306, the example signal data comparator 308, the example input command analyzer 310, and/or the example acoustic test signal controller 316 is/are hereby expressly defined to include a tangible computer readable storage device or storage disk such as a memory, a digital versatile disk (DVD), a compact disk (CD), a Blu-ray disk, etc. storing the software and/or firmware. Further still, the example acoustic signal analysis system 300 of FIG. 3 may include one or more elements, processes and/or devices in addition to, or instead of, those illustrated in FIG. 3, and/or may include more than one of any or all of the illustrated elements, processes and devices.

Figure 4:
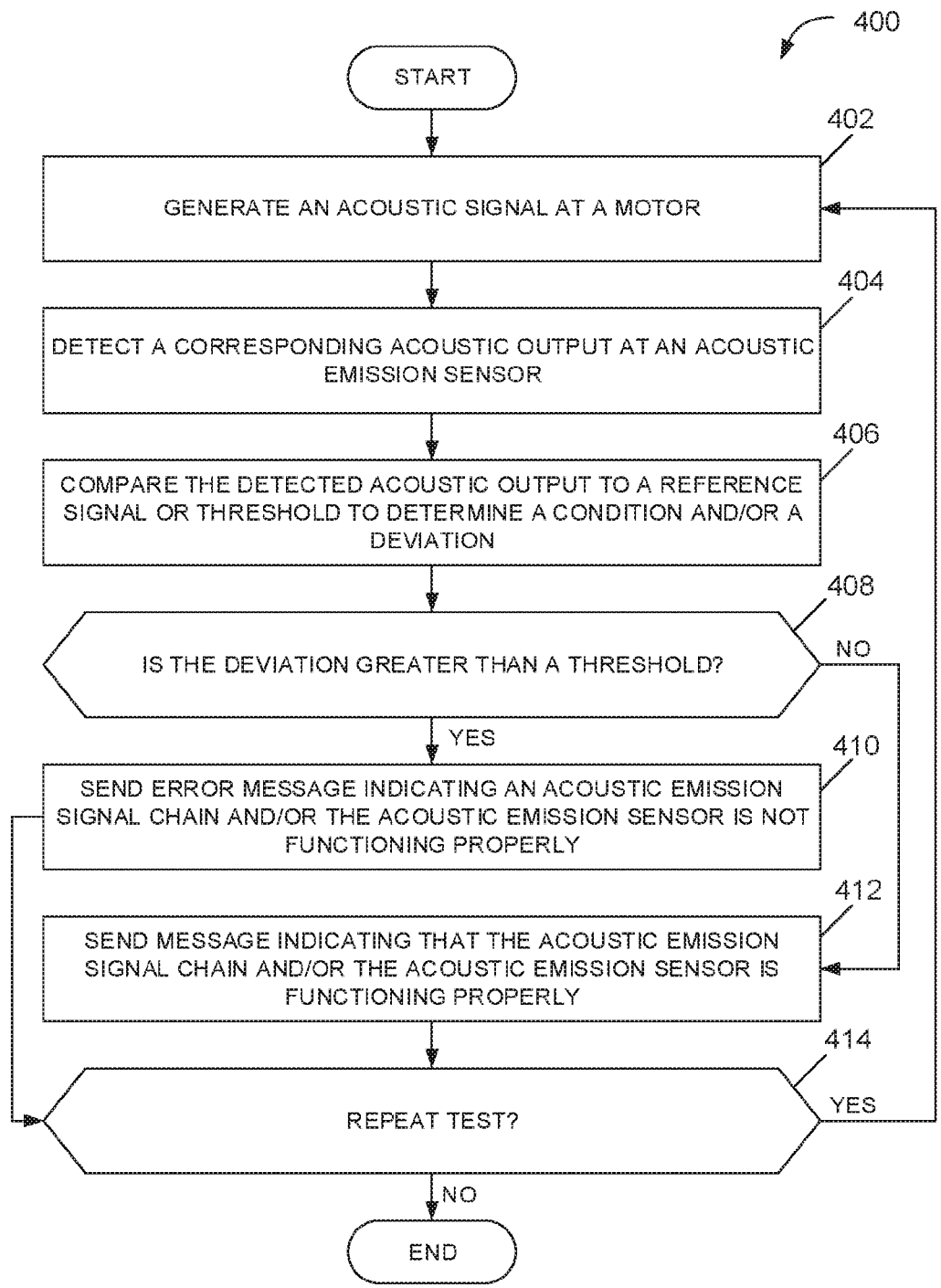
FIG. 4 depicts an example flowchart representative of an example method that may be used to implement the example apparatus described herein.

A flowchart representative of an example method 400 for implementing the acoustic signal analysis system 300 of FIG. 3 is shown in FIG. 4. In this example, the method 400 may be implemented using machine readable instructions that comprise a program for execution by a processor such as the processor 512 shown in the example processor platform 500 discussed below in connection with FIG. 5. The program may be embodied in software stored on a tangible computer readable storage medium such as a CD-ROM, a floppy disk, a hard drive, a digital versatile disk (DVD), a Blu-ray disk, or a memory associated with the processor 512, but the entire program and/or parts thereof could alternatively be executed by a device other than the processor 512 and/or embodied in firmware or dedicated hardware. Further, although the example program is described with reference to the flowchart illustrated in FIG. 4, many other methods of implementing the example acoustic signal analysis system 300 may alternatively be used. For example, the order of execution of the blocks may be changed, and/or some of the blocks described may be changed, eliminated, or combined.

As mentioned above, the example method 400 of FIG. 4 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example method 400 of FIG. 4 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The example method 400 of FIG. 4 begins as a coupling of the acoustic emission sensor 102 to the process control device 110 and/or an accompanying circuit or component corresponding to the acoustic emission sensor 102 is to be verified. In particular, the motor 114 generates a signal that is measured at the acoustic emission sensor 102 so that the measured signal can be compared to a threshold and/or an expected waveform to determine whether the acoustic emission sensor 102 is properly coupled and/or within operating specifications and, thus, operating normally.

According to the illustrated example, an acoustic signal is generated at the motor 214 (block 402). In particular, the example acoustic test signal controller 316 directs the motor 214 to generate a signal to be detected at the acoustic emission sensor 102.

Next, a corresponding acoustic output signal is detected at the acoustic emission sensor 102 (block 404). In some examples, the sensor data analyzer 304 and/or the input command analyzer 310 directs the acoustic emission sensor 102 to enter a measurement mode (e.g., from a standby mode).

In this example, the signal data comparator 308 and/or the sensor data analyzer 304 compares the detected acoustic output to a reference signal or threshold to determine a condition of the acoustic emission sensor 102 and/or a deviation between the detected acoustic output and the reference signal (block 406). In some examples, the signal data comparator 308 compares the detected acoustic output to a threshold (e.g. a numerical threshold). Additionally or alternatively, the signal data comparator 308 compares the detected acoustic output to an expected waveform/signal.

Next, it is determined whether the deviation is greater than the threshold (block 408). In this example, if the sensor data analyzer 304 and/or the signal data comparator determines that this deviation is greater than the threshold (block 408), control of the process proceeds to block 410. Otherwise, the process proceeds to block 412.

If the deviation is greater than the threshold, an error message indicating that the acoustic emission sensor 102, associated structural integrity and/or a signal chain associated with the acoustic emission sensor 102 is not functioning properly is sent (block 410). In particular, the network control interface 306 may be directed to send the error message to the controller 116 and/or the operator workstation 118, for example.

If the deviation is not greater than the threshold, a message indicating that the acoustic emission sensor 102 and/or the signal chain associated with the acoustic emission sensor 102 is functioning properly is sent (block 412). In this example, the network control interface 306 indicates to the controller 116 and/or the operator workstation 118 that the signal chain associated with the acoustic emission sensor 102 is properly operating.

Next, it is determined whether the test of the acoustic emission sensor 102 is to be repeated (block 414). If the test is to be repeated (block 414) control of the process returns to block 402. Otherwise, the process ends. This determination may be based on whether further verification of the testing of the acoustic emission sensor 102 is required and/or when further testing is scheduled.

Figure 5:
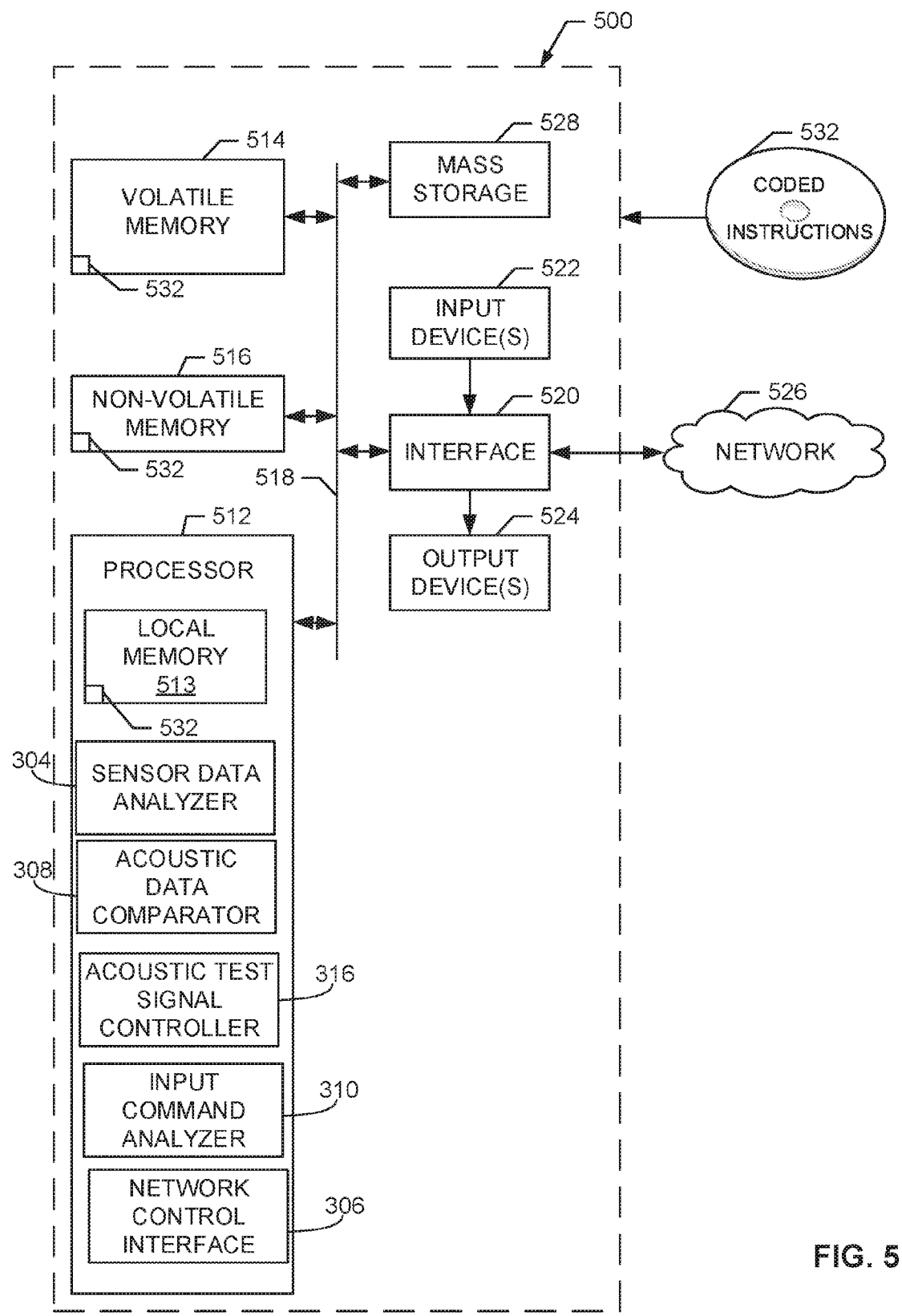
FIG. 5 is a diagram of a processor platform to execute instructions to implement the example method of FIG. 4 and/or the example acoustic test apparatus described herein.

FIG. 5 is a block diagram of an example processor platform 500 capable of executing instructions to implement the method 400 of FIG. 4 and the acoustic signal analysis system 300 of FIG. 3. The processor platform 500 can be, for example, a server, a personal computer, a mobile device (e.g., a cell phone, a smart phone, a tablet such as an iPad™), a personal digital assistant (PDA), a set top box, or any other type of computing device.

The processor platform 500 of the illustrated example includes a processor 512. The processor 512 of the illustrated example is hardware. For example, the processor 512 can be implemented by one or more integrated circuits, logic circuits, microprocessors or controllers from any desired family or manufacturer.

The processor 512 of the illustrated example includes a local memory 513 (e.g., a cache). According to the illustrated example, the processor 512 also includes the example sensor data analyzer 304, the example network control interface 306, the example signal data comparator 308, the example input command analyzer 310, and the example acoustic test signal controller 316. The processor 512 of the illustrated example is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a memory controller.

The processor platform 500 of the illustrated example also includes an interface circuit 520. The interface circuit 520 may be implemented by any type of interface standard, such as an Ethernet interface, a universal serial bus (USB), and/or a PCI express interface.

In the illustrated example, one or more input devices 522 are connected to the interface circuit 520. The input device(s) 522 permit(s) a user to enter data and commands into the processor 512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 524 are also connected to the interface circuit 520 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 520 of the illustrated example, thus, typically includes a graphics driver card, a graphics driver chip or a graphics driver processor.

The interface circuit 520 of the illustrated example also includes a communication device such as a transmitter, a receiver, a transceiver, a modem and/or network interface card to facilitate exchange of data with external machines (e.g., computing devices of any kind) via a network 526 (e.g., an Ethernet connection, a digital subscriber line (DSL), a telephone line, coaxial cable, a cellular telephone system, etc.).

The processor platform 500 of the illustrated example also includes one or more mass storage devices 528 for storing software and/or data. Examples of such mass storage devices 528 include floppy disk drives, hard drive disks, compact disk drives, Blu-ray disk drives, RAID systems, and digital versatile disk (DVD) drives.

Coded instructions 532 to implement the method 400 of FIG. 4 may be stored in the mass storage device 528, in the volatile memory 514, in the non-volatile memory 516, and/or on a removable tangible computer readable storage medium such as a CD or DVD.

From the foregoing, it will be appreciated that the above disclosed methods, apparatus and articles of manufacture enable cost-effective and convenient (e.g., remote) evaluation of process control devices. The examples disclosed herein enable effective evaluation of acoustic emissions sensors by utilizing acoustic sources such as motors, asymmetric motors, haptic motors, speakers, piezoelectric devices, resonators and/or turning forks.

This patent arises as a continuation-in-part of U.S. application Ser. No. 14/992,755, which was filed on Jan. 11, 2016, and U.S. application Ser. No. 15/333,658, which was filed on Oct. 25, 2016, both of which are hereby incorporated by reference in their entireties.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent. While the examples disclosed herein are shown related to process control devices, the examples disclosed herein may be applied to any appropriate acoustic and/or vibration sensor application.

What is claimed is:

1. An apparatus comprising:
an acoustic source acoustically coupled to a device, the acoustic source to generate a test acoustic signal, wherein the acoustic source includes a haptic motor; and
a processor to determine a degradation of an acoustic emission sensor associated with the device based on measuring the test acoustic signal via the acoustic emission sensor, wherein the processor is to compare the measured test acoustic signal to an acoustic reference signal to determine the degradation of the acoustic emission sensor.

2. The apparatus as defined in claim 1, wherein the acoustic reference signal is an expected waveform.

3. The apparatus as defined in claim 1, wherein the haptic motor is overmolded in a polymer.

4. The apparatus as defined in claim 1, wherein the degradation is a condition of a signal chain corresponding to the acoustic source.

5. The apparatus as defined in claim 1, wherein the processor is to compare an amplitude of the measured test acoustic signal to an amplitude of the acoustic reference signal.

6. The apparatus as defined in claim 1, wherein the device is a process control device.

7. An apparatus comprising:
an acoustic source acoustically coupled to a device, the acoustic source to generate a test acoustic signal, wherein the acoustic source is overmolded in a polymer; and
a processor to determine a degradation of an acoustic emission sensor associated with the device based on measuring the test acoustic signal via the acoustic emission sensor, wherein the processor is to compare the measured test acoustic signal to an acoustic reference signal to determine the degradation of the acoustic emission sensor.

8. A method comprising:
generating a test acoustic signal at an acoustic source that is acoustically coupled to a device, wherein the acoustic source includes a motor overmolded in a polymer;
measuring, at an acoustic emission sensor that is operatively coupled to the device, the test acoustic signal;
comparing the measured test acoustic signal to an acoustic reference signal; and
determining, using a processor, a degradation of the acoustic emission sensor based on the comparison of the measured test acoustic signal to an acoustic reference signal.

9. The method as defined in claim 8, further including pulsing the acoustic source.

10. The method as defined in claim 8, further including varying a frequency or amplitude of the test acoustic signal over time.

11. The method as defined in claim 8, wherein determining the degradation of the acoustic emission sensor includes comparing the acoustic signal to a threshold.

12. A tangible machine readable medium comprising instructions, which when executed, cause a processor to at least:
cause an acoustic source to generate a test acoustic signal, wherein the acoustic source is associated with a device, wherein the acoustic source includes a speaker or a motor that is operatively coupled to the device, and wherein the speaker or the motor is encased in a polymer; and
compare the test acoustic signal measured at an acoustic emission sensor associated with the device to an acoustic reference signal to determine a degradation of the acoustic emission sensor.

13. The machine readable medium as defined in claim 12, wherein the instructions cause the processor to vary a frequency or amplitude of the acoustic signal.

14. The machine readable medium as defined in claim 12, wherein the instructions cause the processor to pulse the acoustic source.

15. The machine readable medium as defined in claim 12, wherein the acoustic reference signal includes a signal that was previously measured at the acoustic emission sensor.

16. The machine readable medium as defined in claim 12, wherein the acoustic reference signal includes an expected waveform.

17. The machine readable medium as defined in claim 12, wherein the acoustic source is caused to generate the test acoustic signal based on an indication of at least one of an error or malfunction of the acoustic emission sensor.

* * * * *